United States Patent [19]

Seder et al.

[11] Patent Number: 4,959,048

[45] Date of Patent: Sep. 25, 1990

[54] LACRIMAL DUCT OCCLUDER

[75] Inventors: Edmund V. Seder, Santa Barbara; William F. Sardi, Monrovia, both of Calif.

[73] Assignee: Helix Medical, Inc., Santa Barbara, Calif.

[21] Appl. No.: 297,564

[22] Filed: Jan. 17, 1989

[51] Int. Cl.[5] .............................................. A61M 5/00
[52] U.S. Cl. ........................................ 604/9; 606/107; 623/6
[58] Field of Search ...................... 604/8, 9, 285, 104; 128/897, 898, 831, 843, 341, 303 R

[56] References Cited

U.S. PATENT DOCUMENTS 3,949,750  4/1976  Freeman ...................... 604/294 X
4,660,546  4/1987  Herrick et al. ...................... 128/898
4,764,170  8/1988  Drews .............................. 128/303 R Primary Examiner—Robert A. Hafer
Assistant Examiner—Lynda M. Cofsky
Attorney, Agent, or Firm—Marvin E. Jacobs

[57] ABSTRACT

A reversible, flexible, lacrimal duct occluder is formed of a shaft having a low profile cap at one end and a rounded tip at the other end. At least one, preferably 1-3, conical ranges are forward on the shaft between the ends. The rounded tip enters the punctum followed by leading edge of the range(s) until the occluder bends and enters the horizontal canalicular canal. A series of occluders having 1-3 ranges and varying lengths can be provided to accommodate the different canalicular geometries of different individuals. The occluder is readily inserted without the need to use any special introducer tool and is easily removed from the canaliculus of the patient.

17 Claims, 4 Drawing Sheets

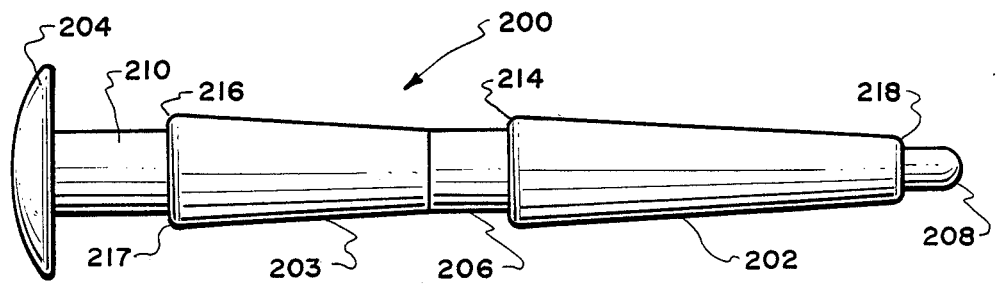
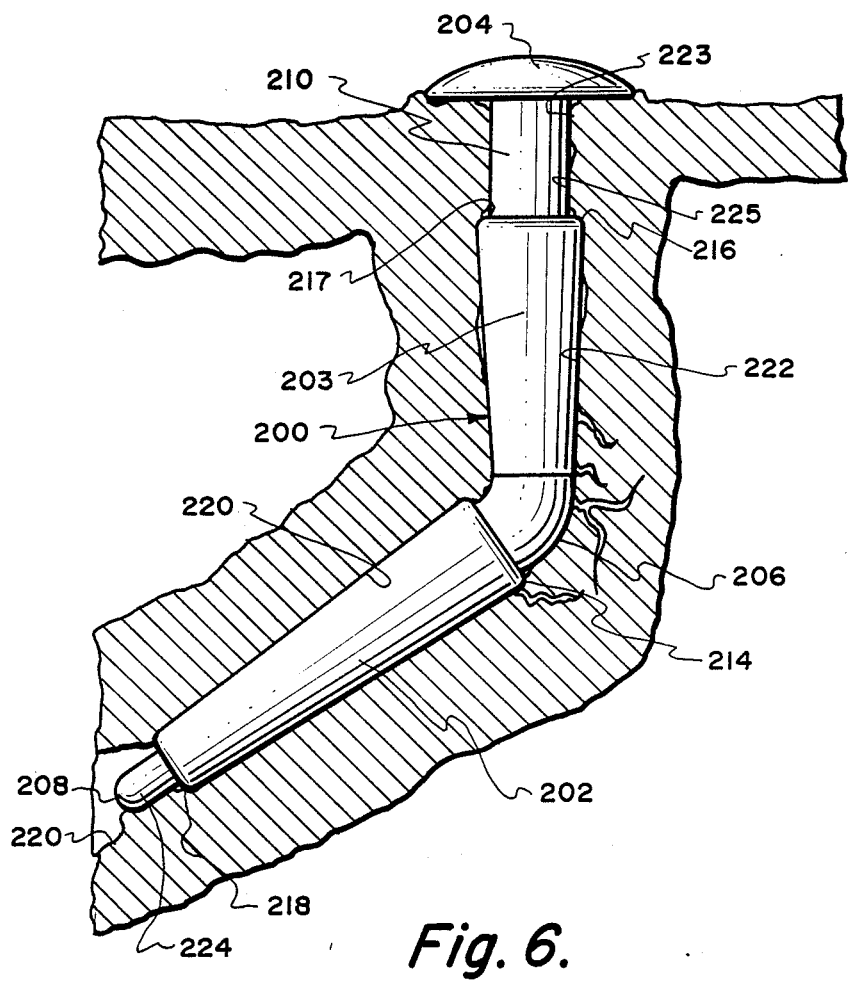
Fig. 5.
Fig. 6.

LACRIMAL DUCT OCCLUDER

DESCRIPTION

TECHNICAL FIELD

This invention relates to a lacrimal duct occluder and, more particularly, this invention relates to a water-insoluble, reversible occluder that can be inserted without predilation of the punctum or the canaliculus.

The occluder of the invention is designed for treatment of dry eye syndrome. Tears in combination with blinking forms a film that has many beneficial affects. Tears contain secretory IgA immunoglobulin which protects the eye from viral or bacterial infection agents. The tear film is complex. It is formed of three layers---lipid, aqueous and mucin. The absence of any of the three layers can cause discomfort or lead to temporary or permanent dry eye syndromes (sicca).

The lipid layer prevents evaporation of tears from the surface of the eye. The aqueous layer which is the major component of the tear layer is secretory by the lacrimal glands. The aqueous layer is responsible for supplying oxygen to the cornea and contains many different chemical components. A decreased supply of lysozyme associated with decreased tear production can lead to several conditions, the most prominent being keratoconjunctivitis sicca. Tears tend to bead up on the cornea in the absence of mucin.

Deficiencies or abnormalities in the layer forming components or other components of the tears can be caused by diseased, or congenital conditions of the glands producing the components or by side effects of drugs utilized to treat other traumatic conditions of the body. Blinking contributes to the formation and maintenance of a continuous tear film on the surfaces of cornea and conjunctiva. Anything that interferes with blinking can lead to drying and in time to diseases of the corneal and conjunctival surfaces.

Many of these conditions are caused by or aggravated by drafts, reading, irritants such as smoke or other gases, bright lights, air conditioning or sleeping. A common over-the-counter drug, chlorpheniramine and other widely used antihistamines, have been shown to decrease tear production in normal individuals. Individuals with dry eye syndrome are more sensitive to irritants and are sensitive to some things that do not affect individuals who do not have dry eyes.

More than 20 external eye diseases and pathologies have been attributed or are related to sicca or dry eye syndrome such as chronic, recurrent and allergic conjunctivitis, blepharitis, contact lens irritation, corneal erosion, incipient corneal graft rejection, recurrent chalzion, pinguecula, corneal ulcers and acute lid abscesses. A major portion of all contact lens problems have been attributed to the quantity and quality of tears by some clinicians.

As many as one-third of adult individuals are affected by chronic dry eye syndrome. Common indications of this condition are eyes that feel sticky, itchy, gritty or burn. Most times the eyes are dry and red, though sometimes the patients' eyes may be watery which is a compensation response to a dry condition. Other problems that have been attributed to dry eye are sinus ailments, hay fever and cold symptoms and recurrent infections.

The usual treatment prescribed for dry eyes by ophthalmologists is the instillation of tear substitutes. Though artificial tears are widely used, some patients experience toxic reaction to the preservative for the tear solution. More viscous tear substitutes that may be indicated for treatment of acute dry eye can cause blurred vision or deposits on the eye lids which are not cosmetically acceptable.

There are several therapies that proceed by mechanically preventing the evaporation of tears such as goggles, transparent wrap shields, moist chamber spectacles, lid taping and bandage contact lenses. All of these devices are uncomfortable and several are expensive and they are unattractive to wear. Humidifiers are useful in alleviating symptoms but can only be utilized in the interior of buildings and do not deal with the cause of the condition.

These early efforts of adding tears or preventing tear evaporation were based on the premise that dry eye syndrome was caused by insufficient tear production. More recent therapies have proceeded on the basis that tear production is adequate in most individuals and that dry eye is caused by excessive tear removal.

Referring now to FIG. 1, tears produced by the lacrimal (tear) glands flow over the eye to form a film and drain through the upper and lower punctum openings 10, 12 located on the upper and lower lids 13, 15 into the canalicular canals 14, 16, the lacrimal sac 18 and nasolacrimal duct 20 into the nose 21. The canals 14, 16 have vertical forward sections 17, 19 and rearward horizontal sections 25, 27. The majority of tears are removed through the lower punctum 12. For many individuals the tear removal or draining system is more efficient than necessary. Certain individuals have overly large puncta or inwardly or outwardly turning eyelids that contribute to excessive tear removal.

There are several alternative ways to occlude the punctum or the canal to stop excessive tear removal. The most drastic way is to permanently block the punctum by stitching or electric or laser cauterization of the opening. These procedures are usually irreversible and, as with any other surgery, there is the cost factor and the risk of infection. In some cases, excess tearing (epiphora) develops after the punctum is closed. It is difficult to reverse the procedure.

Tiny collagen implants have been placed in the upper and lower horizontal canalicular canals. The implants permit only 20–40% of the tears to pass, thus building up a sufficient tear layer on the eyes. These implants can be spontaneously extruded. They are water-soluble and are dissolved and absorbed by the body in 7 to 14 days. Collagen implants are mainly utilized as a testing procedure to determine if the patient is a candidate for permanent surgical closure of the punctum.

A water-insoluble, removable punctum plug or insertion into the punctum opening and vertical section of the canaliculus is disclosed in U.S. Pat. No. 3,949,750 to Freeman and is illustrated in FIG. 2. Freeman is most concerned with spontaneous extrusion of the plug 40 and designed his plug to assure retention. The Freeman plug is a short straight plug having the widest possible diameter for the disc-like head 42 and the blunt tip 44. The punctum must be predilated and the plug must be inserted into the punctum with a special introducer tool. Predilation and forced insertion can cause damage to the tissue surrounding the punctum. Tissue tone is damaged by dilitation. The Freeman plug 40 is designed to be held by gripping the distended sphincter ring 23 of the punctum between the blunt tip 44 and the head 42 of the plug 40. The lowest extension of the Freeman plug is the vertical section 17 of the canaliculus 16. It never enters the horizontal section 25. The Freeman plug is uncomfortable when in place and is still spontaneously extruded in certain patients.

STATEMENT OF THE INVENTION

An improved device for occluding the lacrimal duct is provided in accordance with the present invention. The occluder of the invention is readily inserted into the punctum opening without any dilation of the opening and without the use of any special introducer tool. The occluder is inserted by holding the device with ordinary forceps and inserting it into the punctum opening. The device is effective in occluding the punctum and is comfortable when in place. The occluder of the invention reliably stays in the lacrimal duct but can readily be removed from the punctum when desired.

The cap of the lacrimal duct occluder of the invention has the smallest possible profile and a lacrimal occluder can be inserted into both the upper and lower punctums. Since, in such instances, the two punctums meet during closure of the eyelids, the heads or caps of the occluder will come into contact which helps in maintaining the devices within the punctums and within the canalicular canals.

The lacrimal duct occluder of the invention has the smallest possible diameter along the shaft and terminates in a gradually tapered tip. The tip acts to open the punctum and the gentle ramp or slope of the conical section widens the opening to permit the shaft to enter. The shaft contains at least one and preferable two to three conical segments along the shaft. The shaft is inserted into the vertical canaliculus and bends into the horizontal canaliculus to provide occlusion of the canalicular canal and anchors the occluder without tearing, stretching or irritation of the duct or canal tissue.

The lacrimal occluder of the invention is of low cost and is readily manufactured from available biocompatible materials. A preferred occluder is provided in the form of a very small, flexible, shaped device, formed of inert, non-toxic medical grade silicone elastomer. Due to the variations in the anatomy of individuals, a series of occluder may be provided having different lengths and/or widths to accommodate these anatomical differences.

The lacrimal duct occluder may be coated with lubricant and/or antibiotic before insertion. The lower eyelid is gently grasped to expose the punctum and canaliculus. The lacrimal duct occluder is grasped with forceps at the base or near the tip of the occluder in order to prevent bending of the device as it is inserted. The larger sized occluder is tried first. If it cannot be comfortably inserted, then the next smaller sized occluder is inserted until an occluder is found which enters and is retained in the lacrimal duct. The occluders are usually placed in the two lower canaliculi, but, if desired, can be inserted in all four canaliculi.

The lacrimal duct occluder is easily inserted and can readily be removed by grasping the device with forceps just below the head and gently withdrawing the occluder from the punctum opening. The patient is comfortable after insertion and experiences immediate response to the dry eye condition.

These and many other features and attendant advantages of the invention will become apparent as the invention becomes better understood by reference to the following detailed description when considered in conjunction with the accompanying drawings.

BRIEF DESCRIPTION OF THE DRAWINGS

FIG. 5 is a side view in elevation of a second embodiment of the lacrimal duct occluder of the invention;

FIG. 6 is a schematic view of the second embodiment of the lacrimal duct occluder of the invention;

DETAILED DESCRIPTION OF THE INVENTION

The most important design parameter is the diameter of the occluder and the angle of each conical section. The angle is selected to be shallow enough to allow insertion of the occluder into and through the punctum into the lacrimal canals by means of a gripping tool such as a forcep and yet be sharp enough to cause retention of the occluder in the lacrimal duct. The long length of the flexible occluder also contributes to retention by allowing the forward portion of the tip and conical ramp to bend and enter the horizontal canaliculus.

The shaft has a diameter from about 0.010 to about 0.040 inches. Usually the shaft is about 0.020 inches in diameter and widens to about 0.025 to 0.035 inches along the conical ramps. The tip has a smaller diameter generally from 0.005 to 0.015 inches, typically about 0.010 inches. The tip terminates in a hemispherical end having a diameter equal to the diameter of the shaft of the tip. The tip has a short cylindrical section of from 0.005 to 0.020 inches before it meets the first conical ramp.

The conical sections have conical walls forming an with the shaft of from 2° to about 15°, preferably from 3° to 10°. Each section has a length of about 0.030 to 0.120 inches usually from 0.040 to 0.100 inches. The conical sections occupy a majority of the length of the occluder The length of the occluder is usually at least 0.100 inches and generally need not be longer than 0.400 inches. A length between 0.100 to 0.250 inches satisfies the geometries of most individuals.

The occluder can have one or more conical sections. Usually from 1 to 3 conical ramps. The forwardmost section acts to open the punctum and to help entering and bending into the horizontal canalicular duct. If the occluder first section of the occluder is too short to bend into the horizontal canal, the occluder must be lengthened without increasing the diameter unduly. The second and third sections provide a stepdown so that the diameter of the first section does not increase to a size at which it would irritate the tissue.

Figure 1:
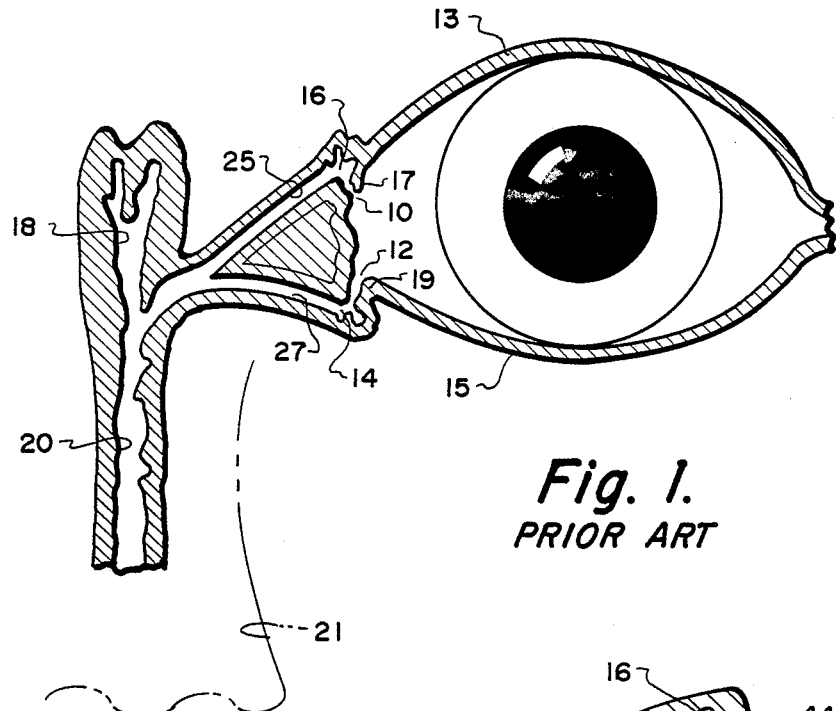
FIG. 1, is a schematic illustration of the prior art lacrimal duct tear drainage system.
Figure 2:
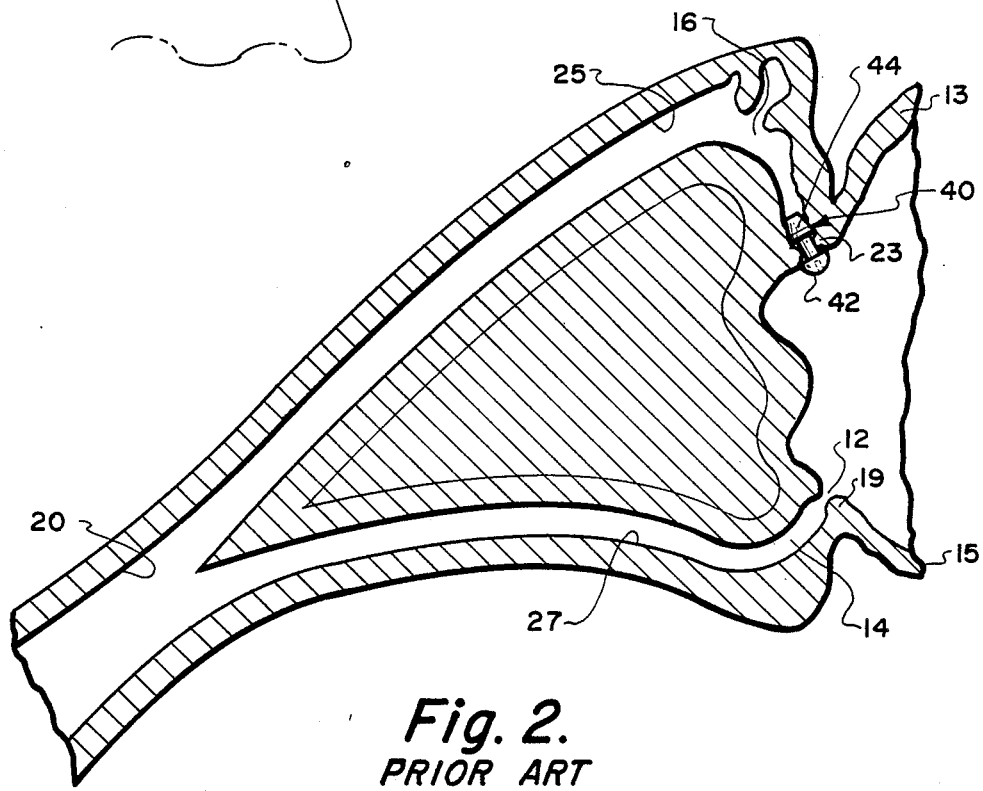
FIG. 2 is a schematic illustration of the implantation of a prior art reversible plug in the vertical canaliculus.
Figure 3:
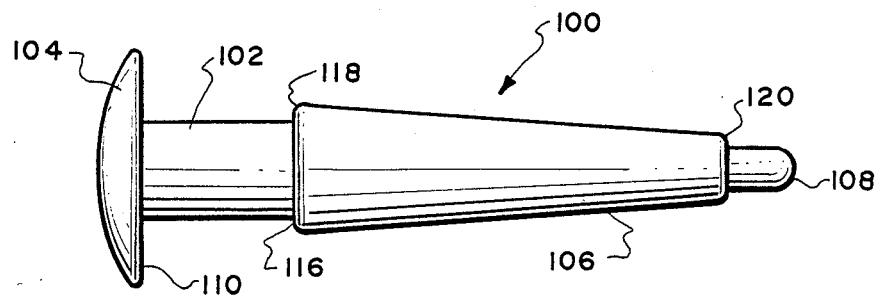
FIG. 3 is a side view in elevation of a first embodiment of the lacrimal duct occluder of the invention.
Figure 4:
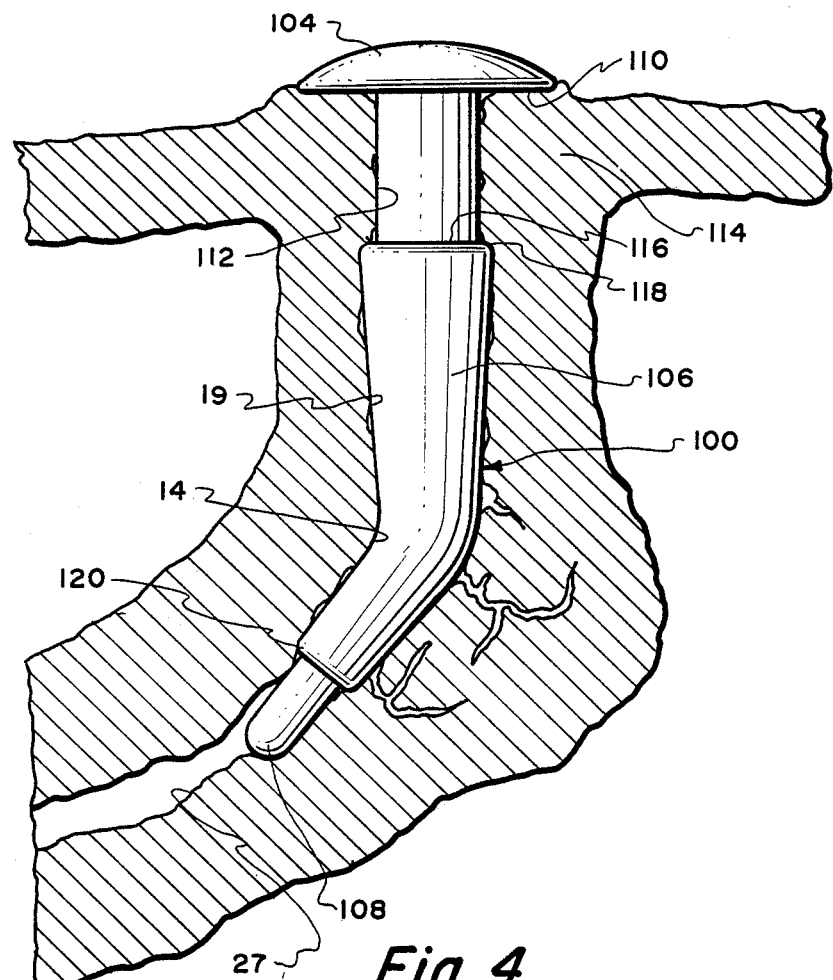
FIG. 4 is a schematic view of the first embodiment of the lacrimal duct occluder shown implanted in a lacrimal duct of a subject.

Referring to FIG. 3, the first embodiment of the lacrimal duct occluder 100 of the invention includes a shaft 102 having a rear end connected to a low profile cap 104 and including a gently sloping conical front section 106. The occluder terminates in a rounded tip 108 of reduced diameter. Referring now to FIG. 4, the tip 108 enters the punctum opening. The punctum opening is widened as the cone section 106 is forced inwardly and bends and engages the wall of the vertical section 19 and the horizontal section 27 of canaliculus 14. The inner surface 110 of the cap 104 engages the outside surface of the punctum. The inner surface 112 of the punctum ring 114 is engaged by the shoulder 116 formed at the end of the conical section 106. The edges 118, 120 of the conical section 106 are preferably rounded to prevent irritation of the tissue.

Referring now to FIG. 5, the second embodiment of a lacrimal duct occluder 200 is longer and includes two sloped ramps 202, 203 rearward of the rounded tip 208. The ramps 202, 203 are separated by a cyclindrical segment 206. A further cyclindrical shaft segment 210 is provided between the cap 204 and the upper end 212 of the upper sloped ramp 203. The upper edges 214, 216 of each ramp 202, 203 are rounded as is the lower edge 218 of the first ramp 202. If the lower ramp was continued up to the top 204, the angle and diameter would be larger than desired and it would be impossible to insert or would be very uncomfortable for the patient.

The mid-segment 206 serves as a bridge or transition between the two ramps 202, 203 and also operates as a hinge as shown in FIG. 6. Since the segment 206 has a smaller diameter than the adjoining increasing and decreasing ramp segments, the occluder preferentially bends at section 206 with the lower end seated in the horizontal canaliculus 220 and the upper end disposed in the vertical canaliculus 222 and punctum 223.

The second occluder 200 is also designed with the comfort of the patient as a paramount criteria. Each of the occluders is inserted with a forceps. The small rounded tip 208 first enters the punctum opening. As the cylindrical tip segment 224 proceeds into the opening, the punctum sphincter ring 225 will gently ride over the rounded lower edge 218 of the first ramp 202 and will proceed up the ramp over the upper rounded edge 214 onto the mid-cylindrical segment 206. At the same time, the tip 208 is proceeding through the vertical canaliculus 223 into the horizontal canaliculus 220.

The punctum 225 will then ride up the second ramp 203 and proceed off the upper rounded edge 216 onto the upper cylindrical 210 and is held between the cap 204 and the shoulder 217. If occluders were placed in both the upper and lower punctum openings, it is apparent that the opposed low profile rounded caps of the occluders can abut when the eyelids are closed without discomfort to the patient and without forcing the occluders through the punctum openings into the lacrimal ducts. The second occluder has two ramps with the same maximum diameter. However, the angles of the ramps are slightly different since the first ramp starts from a smaller initial diameter adjacent to the top section.

Figure 7:
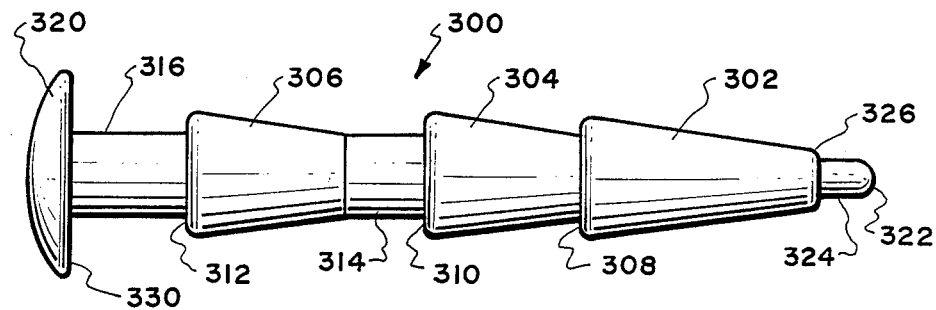
FIG. 7 is a side view in elevation of a third version of the lacrimal duct occluder of the invention; and, FIG. 8 is a schematic view of the third embodiment of the lacrimal duct occluder of the invention.

The third occluder 300 illustrated in FIG. 7 is designed for patients who do not retain the first occluder 100 or the second occluder 200. The third occluder 300 contains three sloped ramps 302, 304, 306 which can have a slightly larger diameter than those utilized in the first and second occluders 100, 200. All the upper edges 308, 310, 312 of the ramps are rounded. The lower ramps 302 and 304 abut each other. A cylindrical transition and hinging section 314 is provided between the ramp 306, 304. An upper cylindrical section 316 is provided between the upper rounded edge 312 and the low profile cap 320.

Figure 8:
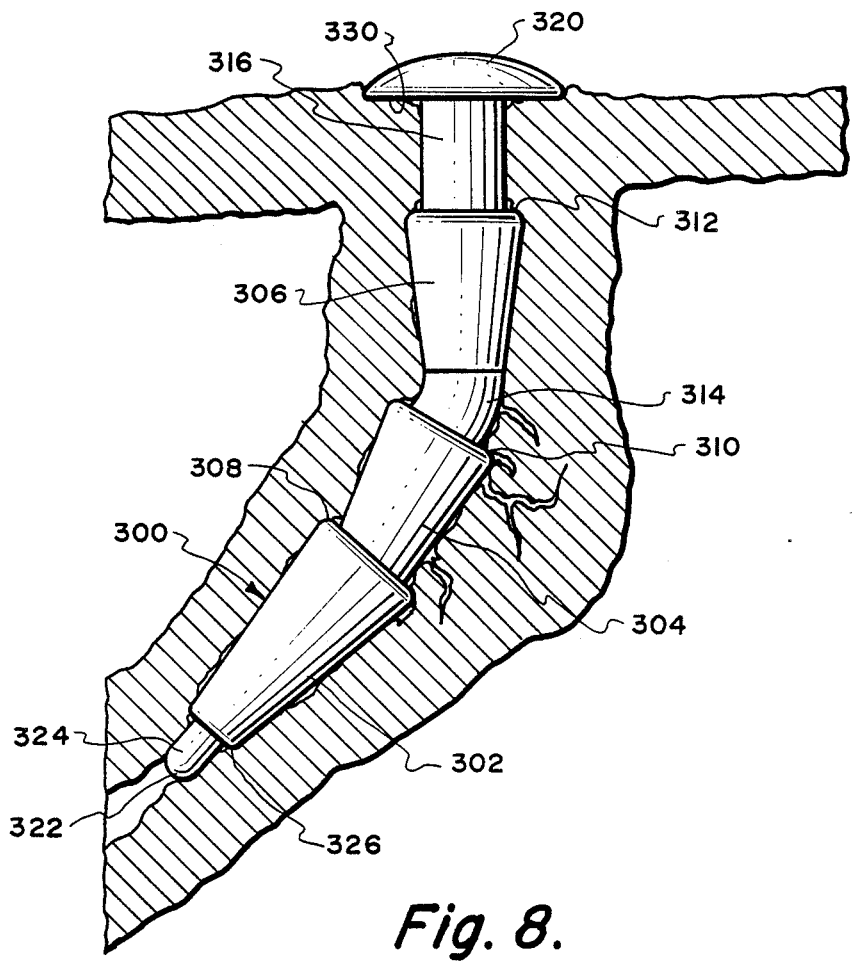

As shown in FIG. 8, the occluder 300 is inserted into the punctum with a forceps, the rounded tip 322 first enters the punctum opening and rides up the cylindrical shaft 324 of the tip 322 onto the rounded lower edge 326 of the lowest ramp 302. As the occluder 300 is pushed into the lacrimal canal, the punctum opening will proceed over the upper rounded edge 308 of the first ramp onto the second ramp 304, over the rounded edge 310 of the second ramp 304, onto the cylindrical shaft section 314 onto the third ramp 306, over the rounded edge 312, onto the cylindrical shaft section 316 until the punctum rests against the lower surface 330 of the low profile cap 320.

The occluder can be made of any inert, non-toxic flexible and pliable material that is compatible with tissue. The preferred material is a medical grade of silicone (polysiloxane) elastomers polymers commonly used for implantable devices.

The lacrimal duct occluder of the invention maintains and improves the amount of tears on the surface of the eye by occluding the tear drains. The device may also be helpful in retarding the loss of eye medications into the nasal passages. Use of the device is indicated for problems, such as dry eyes, which can be improved or resolved by placement of the device within tear drains. Lacrimal duct occluders can be easily removed at any time depending upon the patients, wishes and the judgment of his physician. Some medications, when used topically in the eye or systemically, may cause excess tearing and may require the removal of the device while the medication is being used. Patient intolerance to the device may require the removal of the occluders in some instances. Epiphora (excessive tearing), while generally not experienced, can be a problem in some patients. It is usually resolved quickly without treatment.

The lacrimal duct occluder is tapered profile, provided at least in at least two configurations to occlude the punctum and canaliculus of the eye, thus preventing draining of the lacrimal fluid from the eye. The occluder can be easily removed whenever desired. The different configurations provided by the three occluders are designed to accommodate virtually ever individual irrespective of the variations in anatomy between patients. The lacrimal duct occluder therapy is quickly performed as an office procedure and minimizes the risk of damaging the puncta because no prior dilatation of the puncta is necessary.

The lacrimal duct occluder is indicated for use in the treatment of dry eye caused by such conditions as keratoconjuctivitis sicca, Sjorgren's syndrome, exposure of the eye caused by malpositioned eyelids, medications, age, and contact lenses. Symptoms of dry eye may include such conditions as redness of the eye, burning, tearing, itching, foreign body sensation and contact lens intolerance. Tearing secondary to chronic dacryocystitis with mucopurulent discharge is a relative contraindication to the use of the lacrimal duct occluder. Pre-existing eye infection can also be a contraindication to use of the device.

The Schirmer tear strip test can be run on each patient before and after placement of the device. The procedure can ordinarily be done without anesthetic. However, topical anesthetic eyedrops can be used if desired. The physician may work with the patient in a sitting position, utilizing a slit lamp, or may have the patient lying down with adequate lighting. No prior dilatation of the punctum is necessary. The lacrimal duct occluder is coated with petrolatum-based antibiotic ointment for lubrication and antisepsis. The lower eyelid is gently grasped to expose the punctum and canaliculus. The lacrimal duct occluder is grasped with forceps at the base or near the tip of the occluder in order to prevent bending of the device as it is inserted. The device is carefully and gently inserted into the punctum. The larger sized occluder is tried first. If it cannot be comfortably inserted, than the smaller sized occluder can be used. To remove the device, the occluder is grasped with forceps just below the head, and gently withdrawn.

It is to be realized that only preferred embodiments of the invention have been described and that numerous substitutions, modifications and alterations are permissible without departing from the spirit and scope of the invention as defined in the following claims.

We claim:

1. A reversible, flexible lacrimal duct occluder adapted to enter the punctum opening and block a canalicular canal having a vertical canaliculus connected to a horizontal canaliculus comprising in combination
   a low profile cap having a width larger than the punctum opening;
   a shaft having distal end and a proximal end connected to the cap;
   a rounded tip connected to the distal end of the shaft; and
   at least one rearwardly tapered conical ramp section mounted on said shaft between said ends and the diameter of the ramp being sufficient to block said canal and the distance between said ends being greater than the length of the vertical canaliculus such that the shaft bends and enters the horizontal canaliculus.

2. An occluder according to claim 1 in which the shaft contains 1 to 3 conical sections.

3. An occluder according to claim 2 in which the conical sections are in adjacent positions on the shaft.

4. An occluder according to claim 2 in which two adjacent conical sections are spaced on the shaft whereby the segment on the shaft between said adjacent sections permits preferential bending at the segment.

5. An occluder according to claim 3 in which the tip has a smaller diameter than the adjacent conical ramp.

6. An occluder according to claim 1 in which the conical sections have a gradual taper forming an angle with the shaft from 2° to 15°.

7. An occluder according to claim 6 in which said angle is from 3° to 10°.

8. An occluder according to claim 1 formed of inert, non-toxic, medical-grade polymer.

9. An occluder according to claim 8 in which the polymer is an elastomer.

10. An occluder according to claim 9 in which the elastomer is a silicone.

11. A method of temporarily blocking the lacrimal duct comprising the steps of:
    inserting into the punctum the lacrimal duct occluder of claim 1 with the cap of the occluder seated on the punctum and the tip of the occluder within the horizontal canaliculus;
    maintaining the occluder in the lacrimal canal for a period; and
    removing the occluder from the duct and punctum.

12. A method according to claim 11 in which an occluder is inserted into opposed upper and lower punctums.

13. A reversible lacrimal duct occluder comprising:
    a flexible member having a shaft including a first end and a second end;
    a low profile cap having a larger diameter than the shaft attached to the first end of the shaft;
    a rounded tip attached to the second end of the shaft; and
    a plurality of conical sections gently sloping outwardly toward the cap mounted on the shaft between said ends and the distance between said ends being greater than the length of the vertical canaliculus such that the shaft bends and enters the horizontal canaliculus.

14. An occluder according to claim 13 in which the end of one of the conical sections is spaced a distance from the beginning of the adjacent conical section on the shaft.

15. A reversible, flexible lacrimal duct occluder adapted to enter the punctum opening and block a canalicular canal comprising in combination:
    a cap having a width larger than the punctum opening;
    a shaft having a distal end and proximal end connected to the cap;
    a rounded tip connected to the distal end of the shaft, the distance between said ends being greater that the length of the vertical canaliculus such that the shaft bends and enters the horizontal canaliculus;
    at least two rearwardly tapered conical ramp sections mounted on said shaft between said ends; and
    two of said conical sections being spaced on said shaft from each other to form a segment of said shaft which permits preferential bending of the shaft at said segment.

16. An occluder according to claim 15 in which all the conical sections have substantially the same maximum diameter.

17. An occluder according to claim 16 in which the outer edge of each conical section is rounded.

* * * * *